(12) United States Patent
Yuan et al.

(10) Patent No.: US 7,967,841 B2
(45) Date of Patent: Jun. 28, 2011

(54) METHODS FOR USING LOOPED TISSUE-GRASPING DEVICES

(75) Inventors: Jie Jenny Yuan, Branchburg, NJ (US); Gene W. Kammerer, East Brunswick, NJ (US); An-Min Jason Sung, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 442 days.

(21) Appl. No.: 12/131,182

(22) Filed: Jun. 2, 2008

(65) Prior Publication Data

US 2009/0299407 A1    Dec. 3, 2009

(51) Int. Cl.
*A61B 17/04* (2006.01)
*A61L 17/00* (2006.01)

(52) U.S. Cl. ............................................. 606/228

(58) Field of Classification Search ............. 606/139, 606/144–150, 222–233; 128/898, 899
See application file for complete search history.

(56) References Cited

U.S. PATENT DOCUMENTS

| | | |
|---|---|---|
| 2,998,028 A | 8/1961 | Rohde |
| 3,123,077 A | 3/1964 | Alcamo |
| 3,716,058 A | 2/1973 | Tanner, Jr. |
| 4,069,825 A | 1/1978 | Akiyama |
| 4,669,743 A | 6/1987 | Tipke |
| 5,053,047 A | 10/1991 | Yoon |
| 5,123,913 A | 6/1992 | Wik et al. |
| 5,222,976 A | 6/1993 | Yoon |
| 5,259,846 A | 11/1993 | Granger et al. |
| 5,269,783 A | 12/1993 | Sander |
| 5,330,503 A | 7/1994 | Yoon |
| 5,342,376 A | 8/1994 | Ruff |
| 5,425,747 A | 6/1995 | Brotz |
| 5,584,859 A | 12/1996 | Brotz |
| 5,643,295 A * | 7/1997 | Yoon ............................ 606/151 |
| 5,683,417 A | 11/1997 | Cooper |
| 5,931,855 A | 8/1999 | Buncke |
| 6,083,244 A | 7/2000 | Lubbers et al. |
| 6,241,747 B1 | 6/2001 | Ruff |
| 6,264,675 B1 | 7/2001 | Brotz |
| 6,270,517 B1 | 8/2001 | Brotz |
| 6,358,271 B1 | 3/2002 | Egan et al. |

(Continued)

FOREIGN PATENT DOCUMENTS

EP         1075843 B1     2/2005

(Continued)

OTHER PUBLICATIONS

U.S. Appl. No. 11/801,414, filed May 9, 2007.

*Primary Examiner* — Melanie Tyson

(57) ABSTRACT

A method for repairing friable tissue having a defect therein includes providing a looped barbed suture having a plurality of barbs extending outwardly therefrom along at least a portion of a length thereof, and having first and second ends, first and second end portions and a middle portion therebetween. The first and second ends are fixedly coupled to a single needle, and the plurality of barbs extends outwardly away from the needle. The steps further include placing the looped barbed suture around an outer surface of the friable tissue in a spaced apart configuration and so as to extend across the defect, passing the needle through the friable tissue and around the middle portion of the looped barbed suture one or more times at the middle portion, and removing the needle from the looped barbed suture.

9 Claims, 8 Drawing Sheets

U.S. PATENT DOCUMENTS

| | | |
|---|---|---|
| 6,506,197 B1 | 1/2003 | Rollero et al. |
| 6,599,310 B2 * | 7/2003 | Leung et al. ............. 606/228 |
| 6,773,450 B2 | 8/2004 | Leung et al. |
| 6,848,152 B2 | 2/2005 | Genova et al. |
| 7,056,331 B2 | 6/2006 | Kaplan et al. |
| 2003/0149447 A1 | 8/2003 | Morency et al. |
| 2004/0060409 A1 | 4/2004 | Leung et al. |
| 2004/0060410 A1 | 4/2004 | Leung et al. |
| 2004/0088003 A1 | 5/2004 | Leung et al. |
| 2004/0093028 A1 | 5/2004 | Ruff |
| 2004/0226427 A1 | 11/2004 | Trull et al. |
| 2005/0033367 A1 | 2/2005 | Leung et al. |
| 2005/0203576 A1 | 9/2005 | Sulamanidze et al. |
| 2005/0240224 A1 | 10/2005 | Wu |
| 2005/0267531 A1 | 12/2005 | Ruff et al. |
| 2006/0079935 A1 | 4/2006 | Kolster |
| 2006/0111734 A1 | 5/2006 | Kaplan et al. |
| 2006/0111742 A1 | 5/2006 | Kaplan et al. |
| 2006/0135994 A1 | 6/2006 | Ruff et al. |
| 2006/0135995 A1 | 6/2006 | Ruff et al. |
| 2007/0005109 A1 | 1/2007 | Popadiuk et al. |
| 2007/0005110 A1 | 1/2007 | Collier et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0208377 A1 | 9/2007 | Kaplan et al. |
| 2007/0239207 A1 | 10/2007 | Beramendi |

FOREIGN PATENT DOCUMENTS

| | | |
|---|---|---|
| EP | 1429664 B1 | 3/2007 |
| WO | WO2004/112853 A1 | 12/2004 |
| WO | WO2006/061868 A1 | 6/2006 |
| WO | WO2007/133103 A1 | 11/2007 |

* cited by examiner

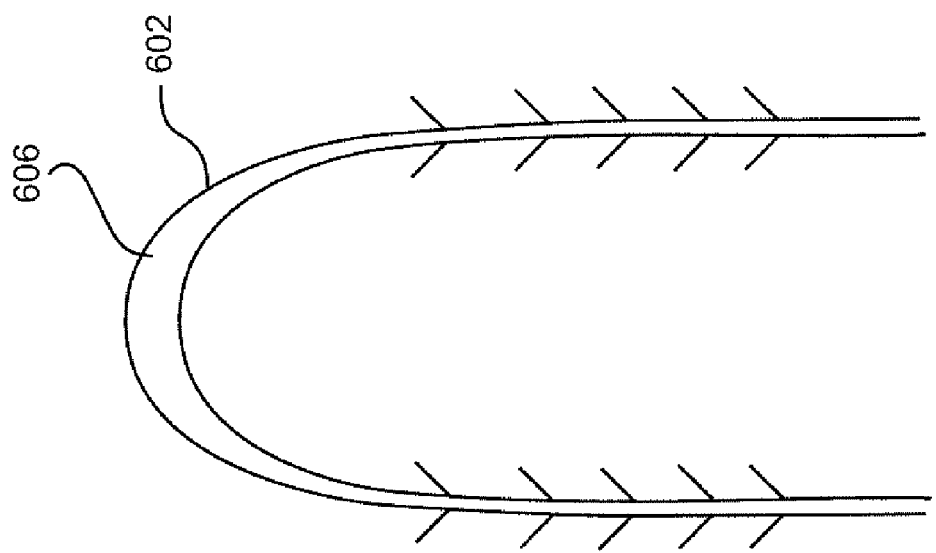
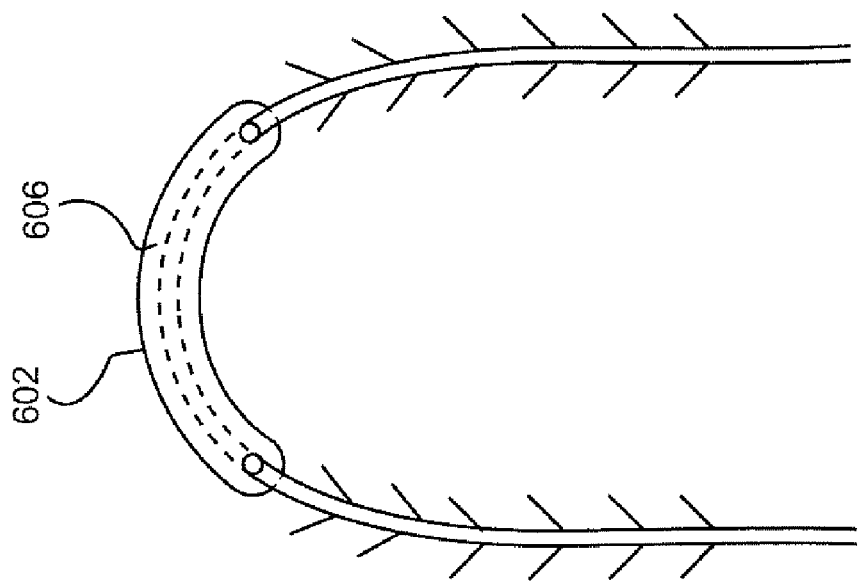

METHODS FOR USING LOOPED TISSUE-GRASPING DEVICES

FIELD

The present invention relates generally to tissue-grasping devices, and more particularly, to surgical methods for using looped tissue-grasping devices.

BACKGROUND

Surgical or accidental wounds are typically closed with a length of filament, commonly referred to as a suture, that is introduced into the tissue by a sharp metal needle attached thereto. Sutures are used to make stitches to close the wound by holding the tissues together for healing and re-growth. Sutures are used in a wide variety of procedures, including surgical procedures for wound closure, to close the skin in plastic surgery, to secure damage or severed tendons, muscles or other internal tissues, and in microsurgery on nerves and blood vessels. Generally, the suture needle is used to penetrate and pass through tissue, pulling the suture through behind it. The opposing faces are then approximated together, the needle removed, and the ends of the suture are tied in a knot to secure it in place. The knotting procedure allows the tension on the filament to be adjusted to accommodate the particular tissue being sutured and to control the approximation, occlusion, attachment or other conditions of the tissue. The ability to control tension is extremely important, regardless of the type of surgical procedure being performed.

Suturing and knot-tying are time-consuming parts of most surgical procedures, particularly in microsurgery and endoscopic surgery where there is limited space to manipulate the suture. For adequate closure of some wounds, the suture material must be of a high tensile strength and multiple stitches must be applied. When the tissue structure is weak or when the closure is in a deep layer, the security of the stitch is especially important. For those tissues that are excessively weak, such as friable organs such as the liver or kidney, suturing is virtually impossible with ordinary sutures, as the tension of the suture in these organs is enough to sever the tissue, which is sometimes referred to as the "cheese wire" effect.

Knots that secure sutures in tissue also present problems. For instance, the tissue is distorted when it is secured by the suture under excess tension from the knots. Localized tensions from the knots also contribute to scar formation. The bulk of the knots is also an impediment to wound healing in internal applications, and/or may be detectable or palpable by the patient through the layers of tissue. For permanent sutures, such as those made from polyesters or polypropylenes, the knots remain indefinitely. Even with absorbable sutures, however, the area around the knots can be sensitive, even for an extended period of time after the knots are gone. Consequently, minimizing the knot mass and size, as well as position, is important to the comfort of the patient. Knots are also believed to be a major source of surgical site infection, as they have the potential to hold bacteria during surgical procedures.

Alternatives to conventional sutures for wound closure are known including fasteners (i.e., staples, clips, tacks or the like) and surface adhesives. Fasteners have relatively high strength and save time, but are not as accurate as sutures and are bulky, and may be painful if they must later be removed. They are also generally unsuitable for deeper layers of tissue, and do not provide the advantage of adjustable tension as do sutures. Adhesives have relatively low holding forces and are unsuitable for many applications.

Recently, barbed sutures have been developed in an effort to avoid the time consuming knot tying steps associated with standard suturing. Multiple barbs project outwardly from the suture shaft in a single direction, and are designed to allow passage of the suture in one direction, but to resist movement or slippage in the reverse direction. Such a unidirectional barbed suture will still require knots at one end (the end toward which the barbs face) to keep it secure. Bi-directional barbed sutures have barbs facing in one direction on one end of the suture and barbs facing in the opposite direction on the other side of the suture. Insertion of this type of barbed suture requires a needle at both ends, and requires that the suture be passed through the tissue in two opposing directions, which is more complicated for a surgeon and limits the applications within which it can be used.

Prior use has also been made of looped sutures, in which both ends of the suture loop are secured to a single needle. Although the tensile strength is increased due to the presence of two filaments, looped sutures still require knotting to anchor the ends of the suture, and require that tension be applied to the suture by another person as the surgeon makes successive stitches. Further, these looped sutures are also subject to slippage within the tissue as they are inserted and/or while securing with knots, and also do not overcome the cheese wire effected when used in friable tissue.

Co-pending U.S. application Ser. No. 11/801,414, filed on May 9, 2007, introduced a novel looped, tissue-grasping suture to overcome some of the disadvantages described above. This co-pending application is hereby incorporated by reference in its entirety. As illustrated in FIGS. 1-3 of that application which are reproduced herein, these looped, tissue-grasping devices 10 include a looped suture filament having a first portion 12 and a second portion 14 having first and second ends 16, 18 respectively that are secured to a needle 20. At least a portion of the first and second portions include a plurality of tissue grasping elements or barbs 22 extending outwardly from the suture shaft in a direction away from the needle. These barbs may be of any suitable configuration and formed by any suitable means, and may project in any manner from the respective strands. For example, they may be aligned along the respective strands in any manner, such as aligned opposite one another as shown in FIGS. 1 and 2, or aligned on a single side as shown in FIG. 3. Any other configuration, such as staggered, random, etc., can also be used so long as the tissue grasping elements of both strands face the same direction, away from the suture needle. For the purposes of this disclosure, the terms "barb" and "tissue grasping" will be used interchangeably, in that either term is intended to mean elements that project outwardly from a suture shaft. These elements may be formed by cutting into the suture shaft, or may be formed by press forming, stamping or the like, and the use of one term or the other is not intended to impart structure or material limitations as to the type of projection and/or type of material used.

Multiple configurations and representative methods for use are described in this co-pending application. However, such described devices can be used in methods and procedures not described therein, and which cannot be accomplished with any previously known devices, including previously known barbed sutures or looped sutures alone.

SUMMARY

A method is provided for repairing friable tissue having a defect. The method includes providing a looped barbed suture having a plurality of barbs extending outwardly therefrom along at least a portion of a length thereof, and having first and second ends, first and second end portions and a middle portion therebetween. The first and second ends are fixedly coupled to a single needle, and the plurality of barbs extends outwardly away from the needle. The method further includes placing the looped barbed suture around an outer surface of the friable tissue in a spaced apart configuration and so as to extend across the defect, passing the needle through the friable tissue and around the middle portion of the looped barbed suture one or more times at the middle portion, and removing the needle from the looped barbed suture. The needle may be passed around the middle portion of the looped barbed suture a plurality of times at successive intervals along a length of the middle portion.

The method may further include, following the passing step, the step of passing the needle through a loop in the looped barbed suture.

The suture may be made of any of the following materials, or combinations of the following materials: polydioxanone, polyglactin, polyglycolic acid, copolymers of glycolide and lactide, polyoxaesters, poly caprolactone, polypropylene, polyethylene, polyvinylidene fluoride (PVDF), ultra high molecular weight polyethylene (UHMWPE), polyesters, polyethylene terephthalate, glycol-modified polyethylene terephthalate, polytetrafluoroethylene, fluoropolymers, and nylons.

In one embodiment, the looped barbed suture includes a widened portion along at least a portion of a length thereof. The widened portion may be along at least a portion of a length of the middle portion, along at least a portion of the first and/or second end portions, and may be integral with the looped barbed suture or a second element that is coupled to the looped barbed suture.

Also provided is a method for repairing friable tissue having a defect therein, including the steps of providing a looped barbed suture having a plurality of barbs extending outwardly therefrom along at least a portion of a length thereof, and having first and second ends, first and second end portions and a middle portion therebetween. The first and second ends are fixedly coupled to a single needle, and the plurality of barbs extend outwardly away from the needle. The method further includes placing a distal portion of the looped barbed suture on a surface of the friable tissue in a spaced apart configuration and across the defect, passing the needle entirely through the friable tissue to a location proximal to the middle portion of the looped barbed suture, passing the needle through the friable tissue and around the middle portion of the looped barbed suture one or more times, and removing the needle from the looped barbed suture. The needle may be passed around the middle portion of the looped barbed suture a plurality of times at successive intervals along a length of the middle portion, and the method may further include, following the second passing step, the step of passing the needle through a loop in the looped barbed suture.

BRIEF DESCRIPTION OF THE DRAWINGS

FIGS. 6*a*-6*c* illustrate alternate exemplary looped barbed suture devices that can be used according to the methods of the present invention.

DETAILED DESCRIPTION

Before explaining the present invention in detail, it should be noted that the invention is not limited in its application or use to the details of construction and arrangement of parts illustrated in the accompanying drawings and description. The invention as illustrated may be implemented or incorporated in other embodiments, variations and modifications, and may be practiced or carried out in various ways.

A looped barbed suture is uniquely suited for repair of friable tissues, where both traditional looped sutures and/or traditional barbed sutures would be unsuitable. When friable tissues such as the liver or spleen need to be repaired, traditional single stranded sutures or traditional looped sutures, when under tension, can easily rip through the weak tissue causing the cheese wire effect referred to above. Additionally, the needle penetration holes can act as a defect to initiate a fracture or crack in the tissue, that can readily further propagate in such friable tissues.

Figure 1:
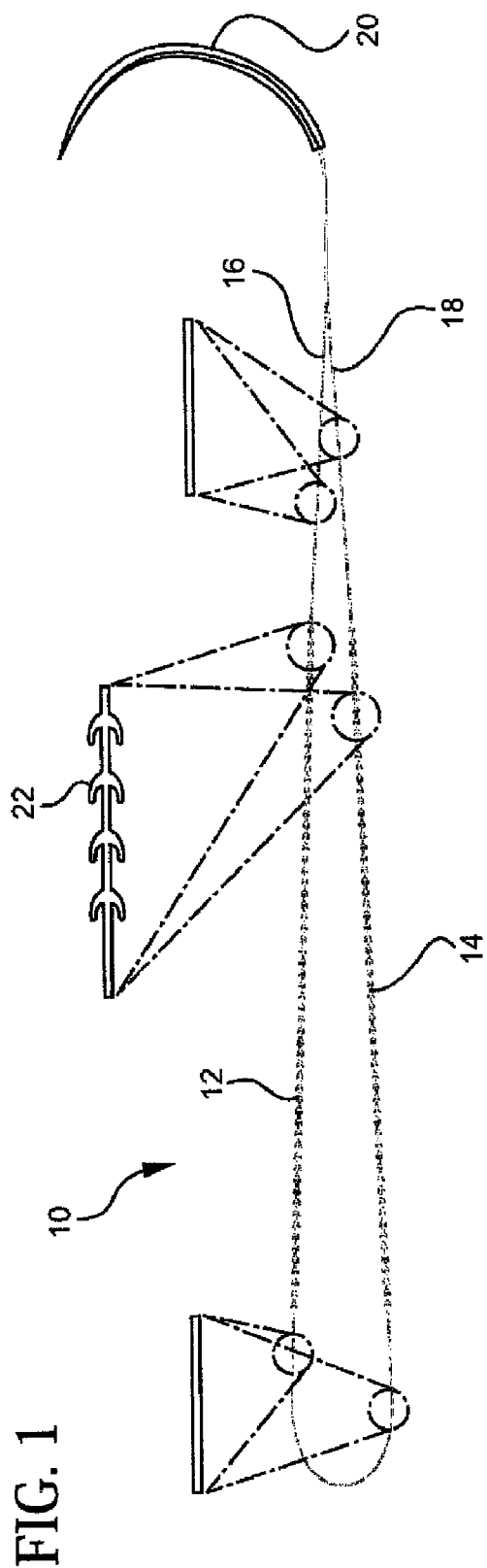
FIGS. 1-3 illustrate exemplary looped barbed suture devices that can be used according to the methods of the present invention.
Figure 2:
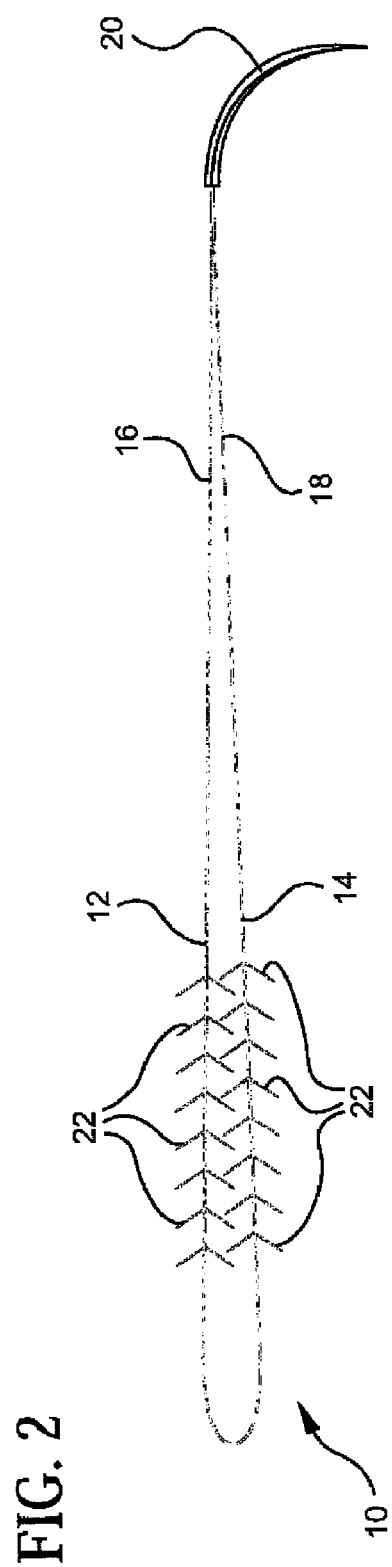
Figure 3:
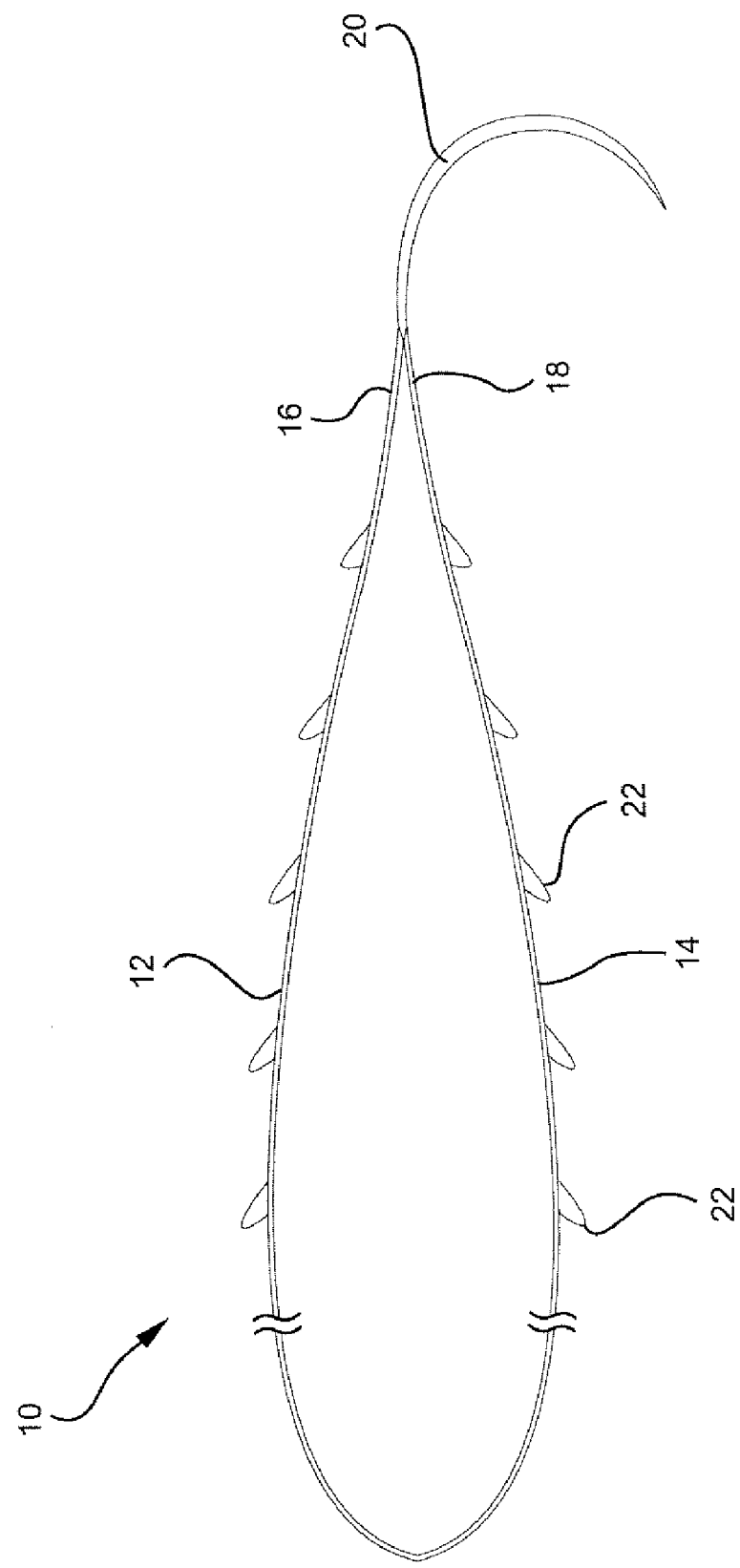
Figure 4A:
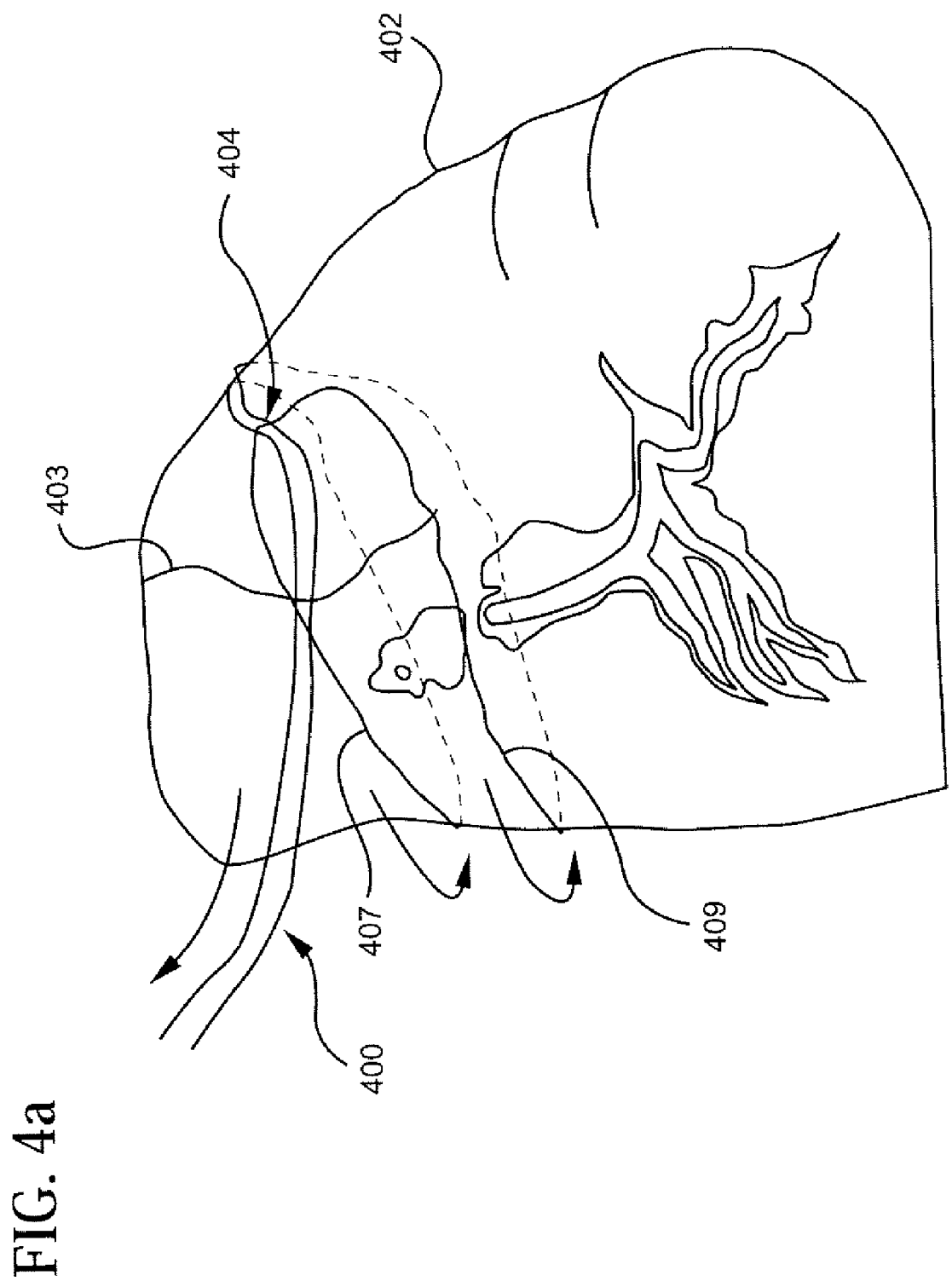
FIGS. 4*a* and 4*b* illustrate one suturing method according to the present invention utilizing a suitable looped barbed suture.

Exemplary procedures for repairing friable tissue with a looped barbed suture according to the present invention will now be described in detail with reference to FIGS. 4*a*, 4*b*, 5 and 5*a*. Although for simplicity these figures do not expressly illustrate barbs or the like, it is to be understood that looped barbed suture devices such as those illustrated in FIGS. 1-3 are to be used. According to one method, the looped barbed suture 400 is first spread open in a spaced apart configuration and passed entirely around the friable organ 402 (i.e., liver or spleen) on its surface and across the wound, incision or other defect 403 as illustrated in FIG. 4*a*. By "spread apart configuration" what is meant is that the first and second end portions 405, 407 (not shown in FIG. 4*a*, but illustrated as reference numerals 16 and 18 in FIGS. 1 and 2) are spaced apart from one another on the surface of the friable tissue as shown in FIG. 4*a*. A middle portion 404 of the looped barbed suture extends between the first and second portions, and is positioned substantially transversely on whole to the first and second portions to enable this spaced apart configuration. The middle portion 404 is spread out on the surface of the friable organ so as to extend across the organ by a length L and, preferably substantially parallel to the defect. The needle and attached ends are then passed through the friable organ and around the looped suture along length L one or more times, and preferably at least 3 or 4 times at succeeding points along the length L as illustrated by reference number 409 in FIG. 4*b*. The final stitch 408 illustrated in FIG. 4*b* may be a reverse locking loop or straight reverse stitch, a standard knot, or any suitable stitch wherein the needle is passed through the friable tissue and back through a loop 410. Due to the barbed nature of the looped barbed suture, the suture will be retained in place and prevented from loosening without the need for additional knotting as with a traditional non-barbed sutures. The ability of the looped barbed suture to retain the illustrated position in the friable organ as described above allows the exerted force to be spread out along a greater length of the suture and over a greater area of the friable tissue, thereby minimizing stress concentrations and reducing the risk of tissue damage due to the "cheese wire" effect that occurs with non-barbed looped sutures.

Another method according to the present invention will now be described in detail with reference to FIG. 5. This method is similar to that described above, but instead of placing the looped barbed suture 500 entirely around the friable tissue, a distal portion 503 is initially laid on the surface (the portion illustrated by the solid lines), with a proximal portion 505 then passed entirely through the tissue (the portion illustrated by the dotted lines). The needle and suture ends are then passed through the friable tissue to a location substantially adjacent to the middle portion 504. As described above, it can then be passed around the looped suture along length L one or more times as described above and shown in FIG. 4b.

Figure 4B:
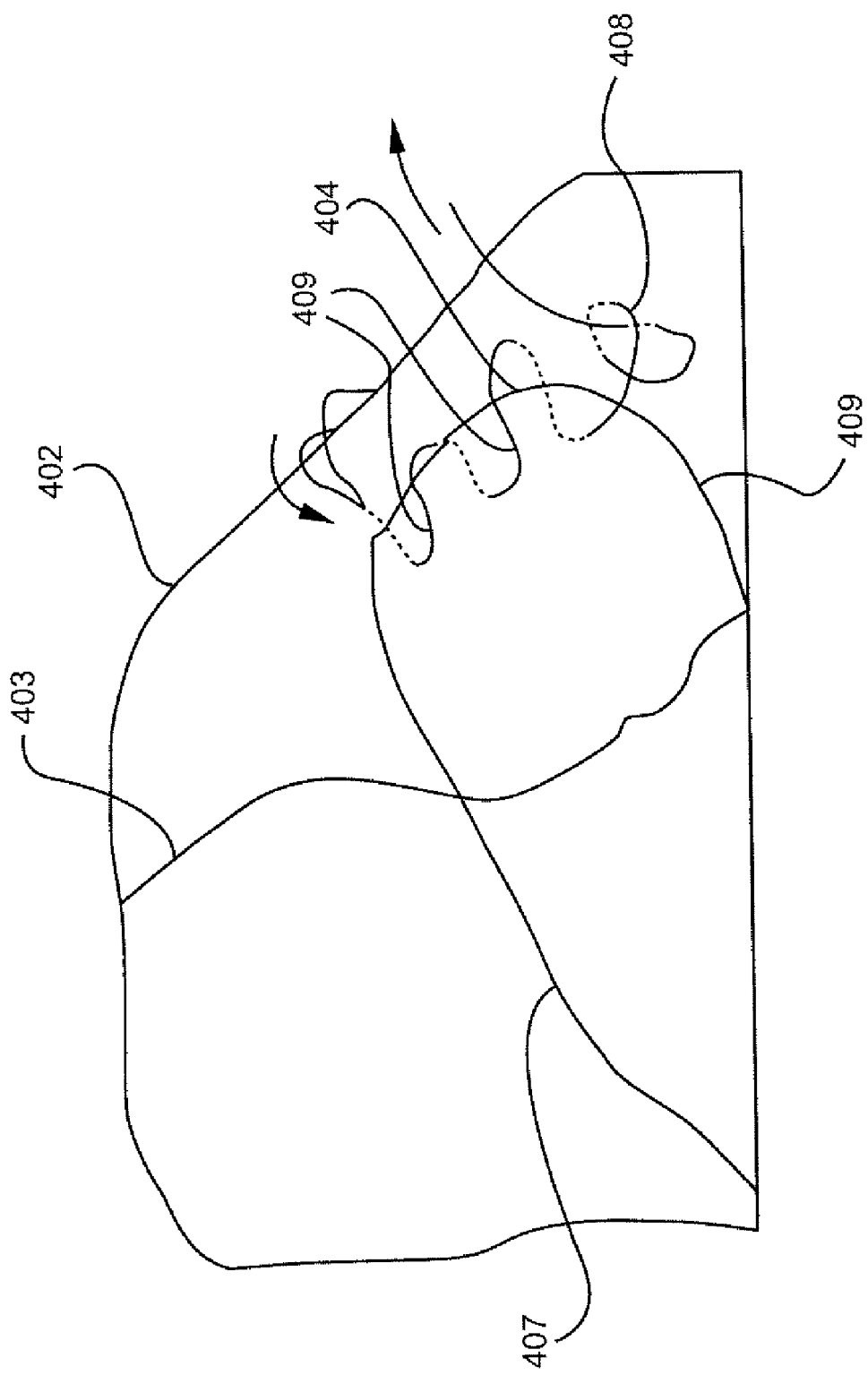
Figure 5:
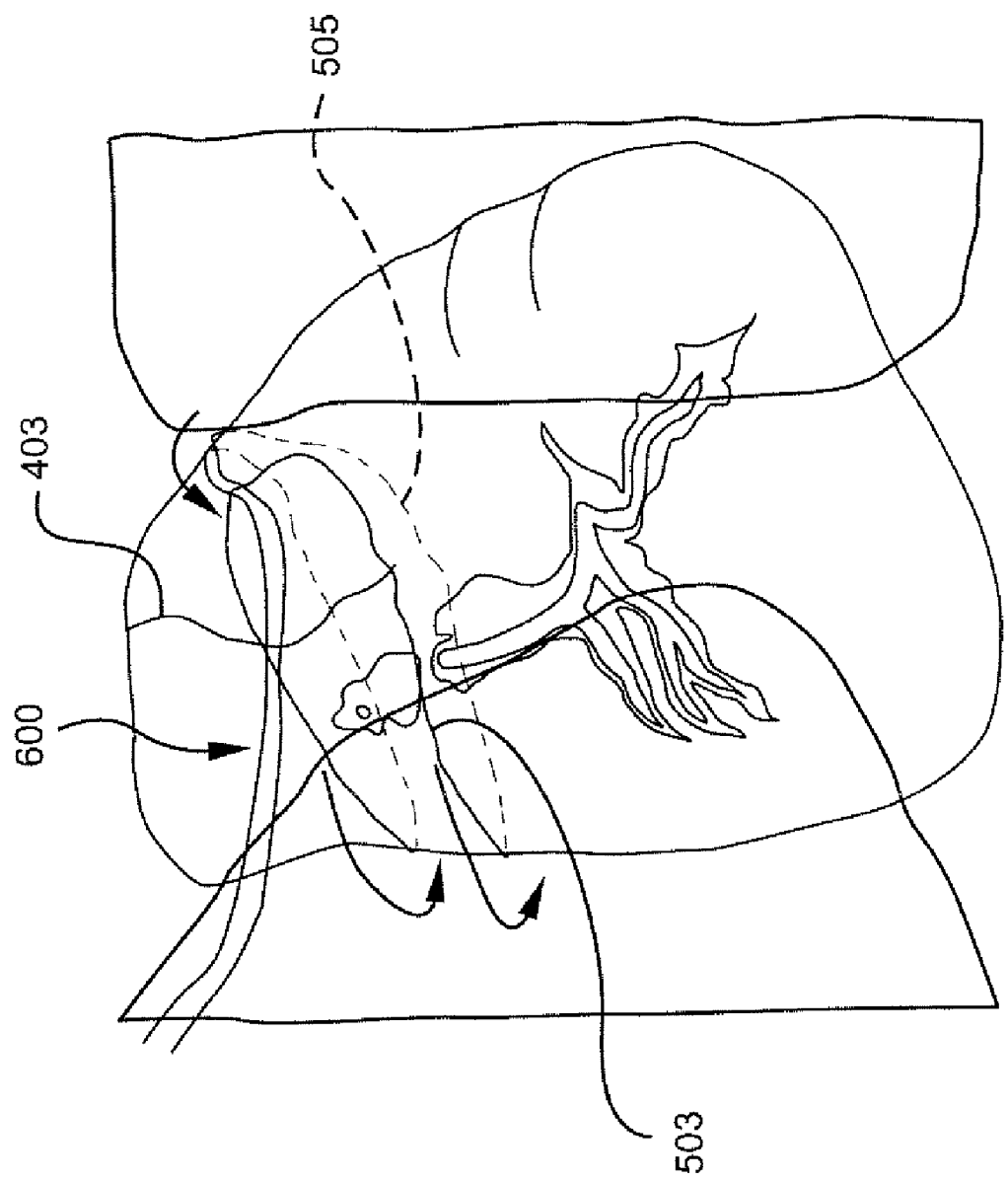
FIGS. 5 and 5*a* illustrate alternate suturing methods according to the present invention utilizing a suitable looped barbed suture.
Figure 5A:
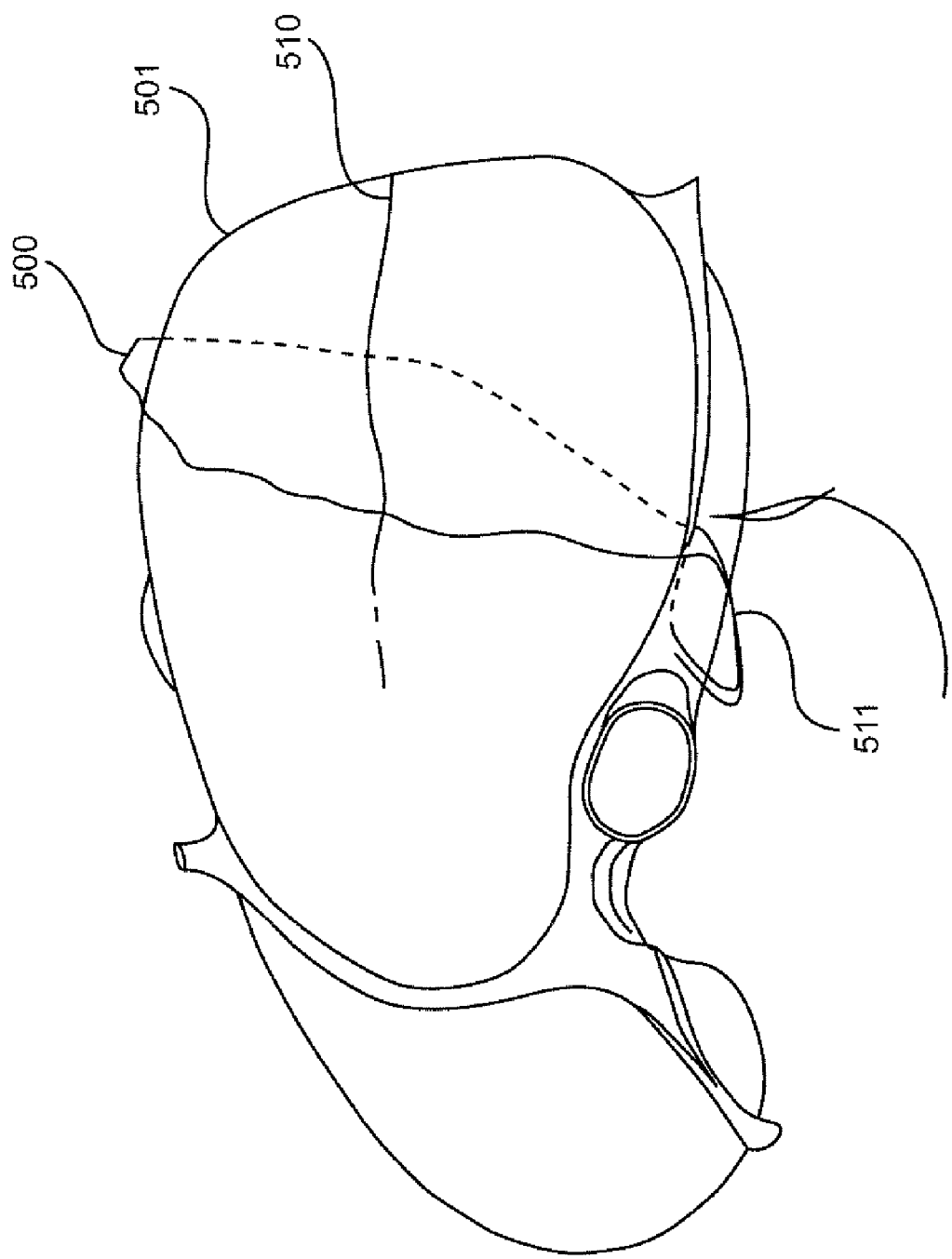

In yet another method illustrated in FIG. 5a, the loop of the looped barbed suture 500 is placed entirely around the friable organ 501, including the defect 510, so that only a single strand extends around the organ rather than two strands as in the methods illustrated in FIGS. 4a, 4b and 5. The needle and suture ends are then passed through the friable tissue and the proximal end of the loop 512 one or more times to hold it in place.

Figure 6C:
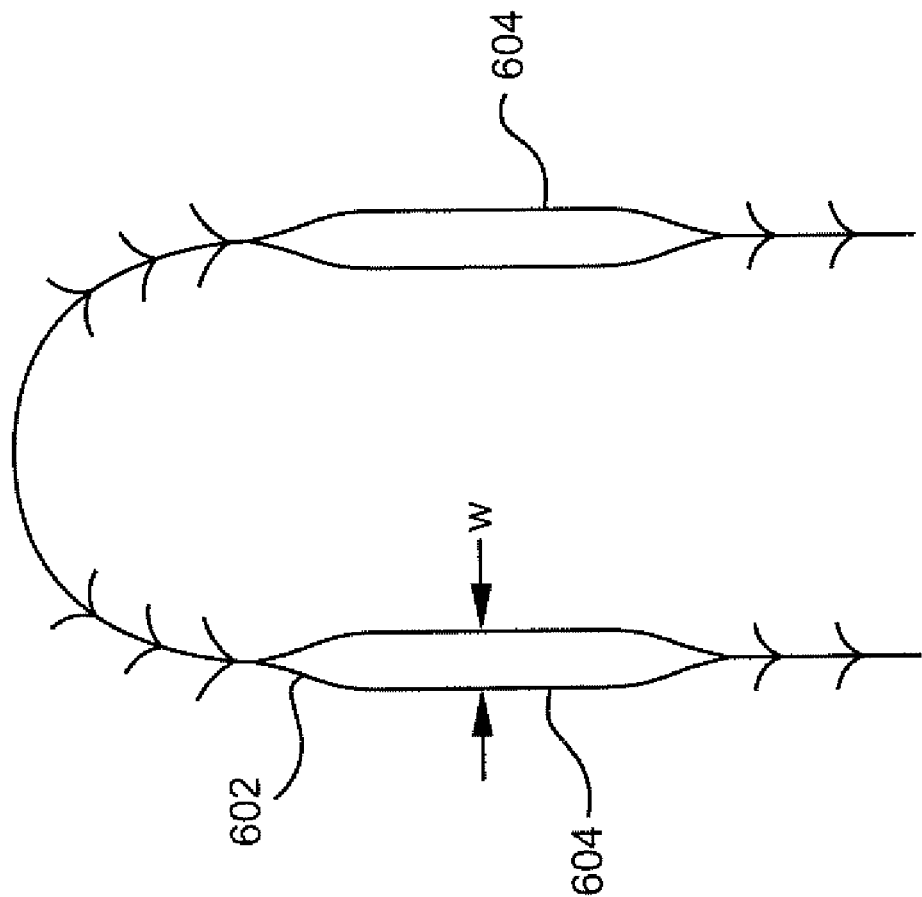

The looped barbed suture described above may also include one or more widened sections 602 along its length as illustrated in FIGS. 6a-6c. The widened sections have a width w greater than a width of the looped barbed suture, which serves to further distribute the forces across a surface of the friable organ. There may be one or more widened sections on sides 604 of the suture as illustrated in FIG. 6c, or the widened section may be along at least a portion of the middle portion 606 as shown in FIGS. 6a and 6b. The widened section may be of any suitable configuration, and may be integrally formed with the suture (i.e., of the same material, as could be the case if the suture was press formed, stamped or the like) as shown in FIG. 6b. The widened portion may also be of a separate material or separate element that is placed around or otherwise coupled to the suture at the desired location as shown in FIG. 6a.

The looped barbed suture may be made of any suitable, bio-compatible material. Suitable polymeric materials include absorbable materials such as polydioxanone, polyglactin, polyglycolic acid, copolymers of glycolide and lactide, polyoxaesters and poly caprolactone, as well as non-absorbable materials such as polypropylene, polyethylene, polyvinylidene fluoride (PVDF), ultra high molecular weight polyethylene (UHMWPE), polyesters, polyethylene terephthalate, glycol-modified polyethylene terephthalate, polytetrafluoroethylene, fluoropolymers, nylons and the like, and combinations thereof, including combinations of absorbable and non-absorbable materials. Preferable materials include, but are not limited to, polypropylene, polydioxanone, UHMWPE and copolymers of poly (glycolide-co-caprolactone).

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

Accordingly, it is not intended that the invention be limited, except as by the appended claims.

What is claimed is:

1. A method for repairing a friable organ having a defect therein, comprising the steps of:
    providing a looped barbed suture having a plurality of barbs extending outwardly therefrom along at least a portion of a length thereof, and having first and second ends, first and second end portions and a middle portion therebetween, wherein the first and second ends are fixedly coupled to a single needle, and wherein the plurality of barbs extend outwardly away from the needle;
    placing the looped barbed suture around and on an outer surface of the friable organ in a spaced apart configuration without penetrating said friable organ with the needle and so as to extend across the defect, wherein the middle portion of the suture is positioned substantially transversely on whole to the first and second portions of the looped barbed suture and positioned substantially parallel to said defect;
    following the placing step, passing the needle through the friable organ in the vicinity of and around the middle portion of the looped barbed suture one or more times at the middle portion; and
    removing the needle from the looped barbed suture.

2. The method according to claim 1, wherein the needle is passed around the middle portion of the looped barbed suture a plurality of times at successive intervals along a length of the middle portion.

3. The method according to claim 2, wherein the suture is comprised of a material selected from the group consisting of polydioxanone, polyglactin, polyglycolic acid, copolymers of glycolide and lactide, polyoxaesters, poly caprolactone, polypropylene, polyethylene, polyvinylidene fluoride (PVDF), ultra high molecular weight polyethylene (UHMWPE), polyesters, polyethylene terephthalate, glycol-modified polyethylene terephthalate, polytetrafluoroethylene, fluoropolymers, nylons, and combinations thereof.

4. The method according to claim 2, wherein the looped barbed suture further comprises a widened portion along at least a portion of a length thereof.

5. The method according to claim 4, wherein the widened portion is along at least a portion of a length of the middle portion.

6. The method according to claim 4, wherein the widened portion is along at least a portion of the first and/or second end portions.

7. The method according to claim 4, wherein the widened portion is integral with the looped barbed suture.

8. The method according to claim 4, wherein the widened portion is a second element coupled to the looped barbed suture.

9. The method according to claim 1, wherein the friable organ is a liver.

* * * * *